(12) United States Patent
Chen et al.

(10) Patent No.: US 7,632,526 B2
(45) Date of Patent: Dec. 15, 2009

(54) HEALTH SUPPLEMENT FOR LOWERING PLASMA GLUCOSE AND PLASMA TRIGLYCERIDE

(75) Inventors: Jan-Kan Chen, Taipei (TW); Ruey-Yu Wang, Taipei (TW)

(73) Assignee: Formosa Biomedical Technology Corp., Taipei (TW)

( * ) Notice: Subject to any disclaimer, the term of this patent is extended or adjusted under 35 U.S.C. 154(b) by 28 days.

(21) Appl. No.: 11/907,023

(22) Filed: Oct. 9, 2007

(65) Prior Publication Data

US 2009/0092695 A1    Apr. 9, 2009

(51) Int. Cl.
*A01N 65/00*    (2006.01)
(52) U.S. Cl. ...................................................... 424/725
(58) Field of Classification Search ........................ None
See application file for complete search history.

(56) References Cited

U.S. PATENT DOCUMENTS

2002/0192314 A1* 12/2002 Cho et al. ................... 424/766

\* cited by examiner

*Primary Examiner*—Michael V Meller
(74) *Attorney, Agent, or Firm*—Bacon & Thomas, PLLC

(57) ABSTRACT

A kind of health supplement for lowering plasma glucose and plasma triglyceride is prepared from a mixture of dried grape skins with the flesh removed, dried grape seeds and dried grape stems, and the mixture is ground into fine powder (termed 3SG powder) according to a ratio of volume between the grape skins, the grape seeds and the grape stems found in naturally available grapes; upon treatment of the 3SG powder with ethanol, the intracellular lipid-soluble flavonoids of the 3SG powder are released to give rise to the health supplement which functions include to lower plasma glucose and plasma triglyceride, as well as to attenuate anomalous energy metabolism in diabetic, hyperglycemic, and hyperlipidemic people.

1 Claim, 12 Drawing Sheets

HEALTH SUPPLEMENT FOR LOWERING PLASMA GLUCOSE AND PLASMA TRIGLYCERIDE

BACKGROUND OF THE INVENTION

1. Field of the Invention

The invention relates to a health supplement for lowering plasma glucose and plasma triglyceride, and more particularly to a health supplement resulted from releasing cell contents from a mixture of ground-up grape skin, ground-up grape seeds, and ground-up grape stems.

2. Description of the Prior Art

Diabetes is a metabolic disorder characterized in that the pancreas in an afflicted person does not secrete sufficient insulin, consequently impeding the ability of body tissues to utilize sugars in his body, and this leads to elevated plasma glucose and the excretion of glucose in urine; the main symptoms of diabetes are increased thirst (thus increased fluid intake), increased appetite, frequent urination, fatigue, and weight loss.

Diabetes is listed as one of the most dangerous illnesses in that chronic high plasma glucose could lead to other implications, such as kidney diseases, retinal diseases, stroke, and cardiovascular diseases. Therefore, treatments of diabetes mainly focus on improving the metabolism, as well as lowering the plasma glucose and plasma triglyceride of the afflicted patients, so that the implications of other diseases may be prevented.

Among the natural plants, grapes are rich in various flavonoids, which include resveratrol and its glycosides, and are beneficial in alleviating the symptoms of diabetes, as well as lowering plasma glucose and plasma triglyceride. Therefore, if grapes may be made into a natural health supplement by removing its flesh and taken regularly, it may help relieve the symptoms resulted from abnormal metabolism, such as high plasma glucose and high plasma triglyceride.

SUMMARY OF THE INVENTION

A primary objective of the invention is to propose a health supplement for lowering plasma glucose and plasma triglyceride; using a mixture of grape skin with the flesh removed, grape seeds, and grape stems as the raw material, and then grind the mixture into fine powder (abbreviated as 3SG powder hereafter) according to a ratio of volume between the grape skin, the grape seeds, and the grape stems found in naturally available grapes. The cell contents in the 3SG powder are released in order to give rise to the health supplement (abbreviated as 3SGA powder hereafter), which may lower plasma glucose and plasma triglyceride, as well as alleviating the symptoms of diabetes such as increased appetite, increased fluid intake, and weight loss.

BRIEF DESCRIPTION OF DRAWINGS

The structure and the technical means adopted by the present invention to achieve the above and other objectives can be best understood by referring to the following detailed description of the preferred embodiments and the accompanying diagrams, wherein.

In order to indicate statistically significant differences in all of the drawings, the symbol "**" is used to represent $p<0.01$, whereas the symbol "*" is used to represent $p<0.05$.

DETAILED DESCRIPTION OF PREFERRED EMBODIMENTS

Figure 1:
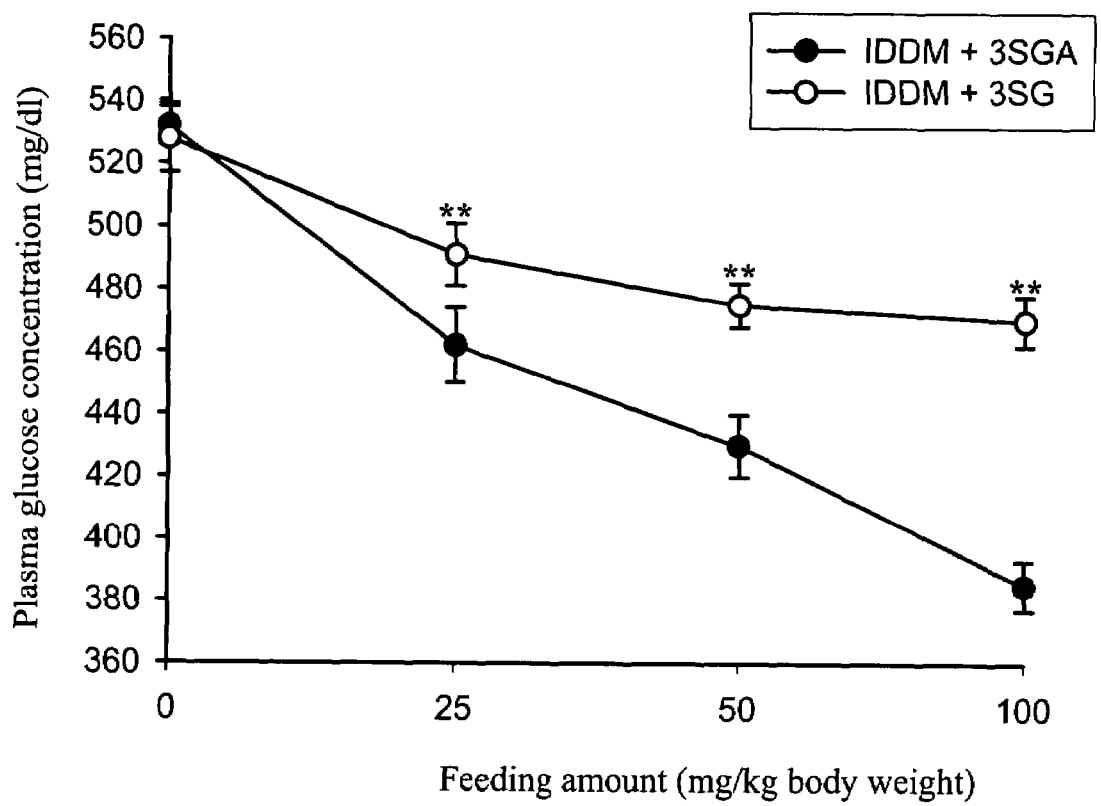
FIG. 1 is a diagram that shows the comparison of plasma glucose levels between sick IDDM rats that took different dosages of 3SG powder and 3SGA powder.

The health supplement disclosed in the invention is made from a material selected from grape skin, grape seeds, grape stems, or a mixture thereof, from which the fruit flesh has been removed; the material is further processed in order to result in the health supplement that may lower plasma glucose and plasma triglyceride. Because the health supplement is made from the natural material, and does not have adverse side effects or toxicity, the health supplement may be taken in order to alleviate the symptoms of diabetes, high plasma glucose, and high plasma triglyceride.

The health supplement for lowering plasma glucose and plasma triglyceride disclosed in the invention is made via a method comprising the following steps:

a. Using a material selected from grape skin, grape seeds, grape stems, or a mixture thereof, from which residual fruit flesh and foreign substances have already been removed; the material is rinsed, dried, and then ground into a dark purple powder (abbreviated as the 3SG powder).

Use grape skin, grape seeds, and grape stems in a ratio of volume found in naturally available grapes as the material, and rinse the material with fresh water three times in order to remove foreign substances and residual fruit flesh, then the material is left in a drying oven at 45° C. for three days until it becomes crisp. Subsequently, the dried material is ground into powder in an automatic grinding machine, and has coarser xylem fiber removed by using a fine sieve. Finally, a dark purple powder is obtained, and is called the 3SG powder, wherein the 3S stands for skin, seed, and stem, and G stands for grape.

b. Ethanol is added to the 3SG powder obtained in the step (a) at a ratio of 1 ml of ethanol to every 1 g of the 3SG powder;

the 3SG powder and ethanol are mixed together and stirred in order to release lipid-soluble flavonoids from cells in the 3SG powder;

Because plant cells are enclosed by cell walls made of cellulose, it prevents cell contents within the plant cells from being easily absorbed into human digestive tracts. To solve this problem, the 3SG powder is immersed in a proportionally equal amount of ethanol in this invention. In a preferred embodiment of the invention, 99.8% ethanol is used to immerse the 3SG powder for one hour, so as to release lipid-soluble flavonoids from cells in the 3SG powder into the ethanol solution.

c. Allowing ethanol in the mixture resulted in the step (b) to completely evaporate, so that the flavonoids that have been released into the ethanol solution may be adsorbed to surfaces of the 3SG powder, thereby obtaining the health supplement of the invention.

After the lipid-soluble flavonoids in the 3SG powder have been released into the ethanol solution, the mixture is left in an environment of negative pressure at 37° C. for two days, so that ethanol may evaporate completely. In the process, the flavonoids that have been released into the ethanol solution is allowed to be absorbed to the external surface of the 3SG powder, thereby giving rise to the 3SGA powder, wherein the "A" on "3SGA powder" stands for the "3SG powder" having been processed by alcohol.

The 3SGA powder of the invention may be easily absorbed into human digestive tracts because most of the flavonoids had been released from the cells in the 3SG powder and absorbed to the external surface of the 3SG powder, and may lower plasma glucose more effectively than the 3SG powder.

A. Animal Experiments to Show the 3SGA Powder Provided Function to Reduce Plasma Glucose and Plasma Triglyceride 1. Animals used to test levels of plasma glucose and plasma triglyceride:

Normal SD (Sprage-Dawley) rats, normal C57BL/6 rats, sick Insulin-Dependent Diabetes Mellitus rats (abbreviated as sick IDDM rats hereafter), and sick Non-Insulin Dependent Diabetes Mellitus rats (abbreviated as sick NIDDM rats hereafter).

2. Methods of feeding the 3SG powder and the 3SGA powder:

100 mg of 3SG powder or 3SGA powder is evenly mixed with 1 ml sterilized water, and the resulted mixture is fed to the animals via a gastric tube every 8 hours (8 AM, 4 PM, and 12 AM, three times daily). The amount fed to the animals is 25 mg/kg BW (25 mg of mixture to every kg of body weight), 50 mg/kg BW, or 100 mg/kg BW.

Between the time of feeding the 3SG powder or the 3SGA powder, the animals may eat freely, but the animals are put on fasting for 24 hours before drawing blood and testing plasma glucose and plasma triglyceride levels.

3. Methods for testing levels of plasma glucose:

On the night prior to the experiments, the normal SD rats, the sick IDDM rats, and the sick NIDDM rats are put on fasting. On the next day, the animals are anesthetized with pentobarbital 30 mg/kg BW via intraperitoneal injection. 0.2-0.6 ml of blood samples are drawn from the rats on empty stomach, then the 3SG powder or the 3SGA powder is fed into the stomach of the animals. Separate blood samples are drawn 60 mins, 90 mins, and 120 mins after feeding, and all of the blood samples are centrifuged (13,000 rpm, 3 mins) in order to separate plasma from blood cells. 10 µl-samples are taken from the plasma at the upper layer, to which 1 ml of reactants from the glucose kit is added, the mixture is then mixed evenly before being allowed to react in a 37° C. water bath for 10 mins. Subsequently, a plasma glucose analyzer (Quick-Lab, Chemistry Analyzer) is used to calculate the level of plasma glucose (mg/dL) according to differences in light absorption and comparison with the standard.

B. Short Term Tests

1. Changes in plasma glucose and plasma triglyceride levels after the sick IDDM rats had taken the 3SG powder and the 3SGA powder:

The sick IDDM rats are divided into eight groups, and there are eight rats in each group. Four groups of the sick IDDM rats are fed with the 3SG powder of 0, 25, 50, or 100 mg/kg BW in dosage. The other four groups of the sick IDDM rats are fed with the 3SGA powder in 0, 25, 50, or 100 mg/kg BW in dosage.

Figure 2:
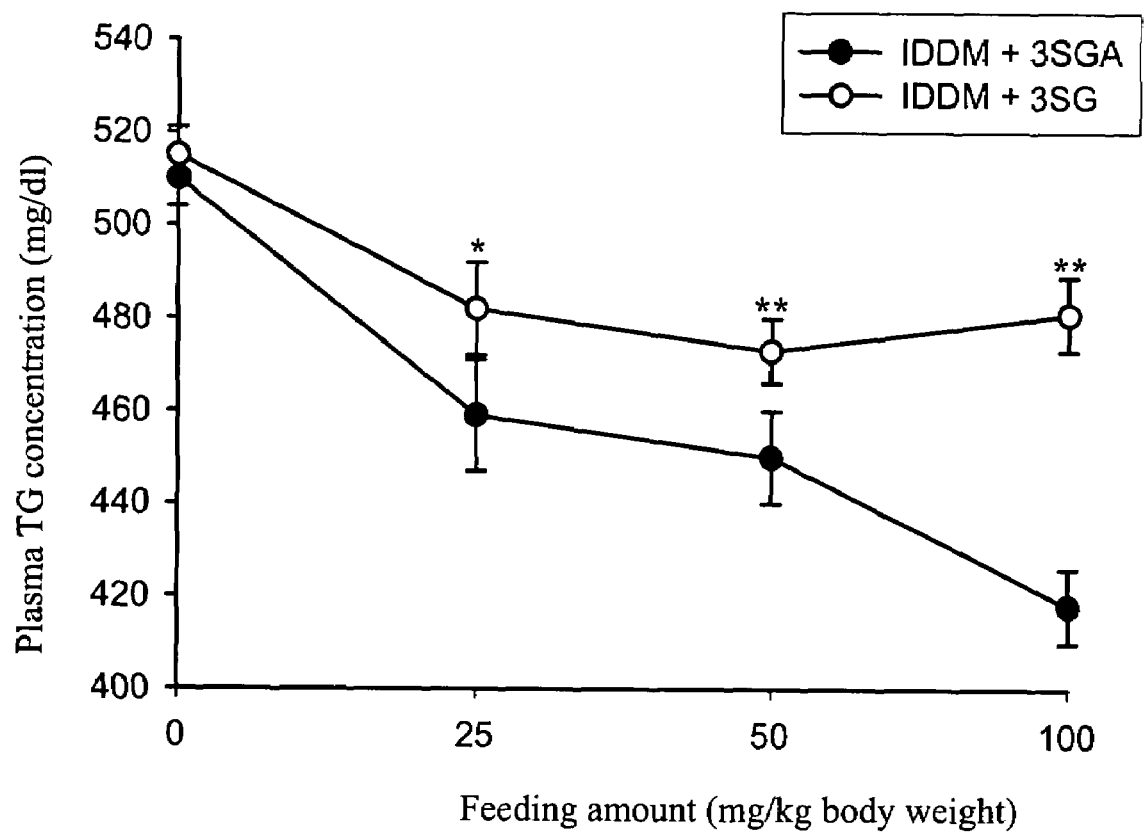
FIG. 2 is a diagram that shows the comparison of plasma triglyceride levels between sick IDDM rats that took different dosages of 3SG powder and 3SGA powder.

After feeding, blood samples are drawn from each group of rats to test the levels of plasma glucose and plasma triglyceride. The changes in the levels of plasma glucose of rats after taking the 3SG powder and the 3SGA powder is shown in FIG. 1, while the changes in the levels of plasma triglyceride of rats after taking the 3SG powder and the 3SGA powder is shown in FIG. 2. It can be observed from FIGS. 1 and 2 that the levels of plasma glucose and plasma triglyceride in the sick IDDM rats had been lowered, but the feeding of the 3SGA powder is more effective for lowering the levels of plasma glucose and plasma triglyceride than that of the 3SG powder.

Figure 3:
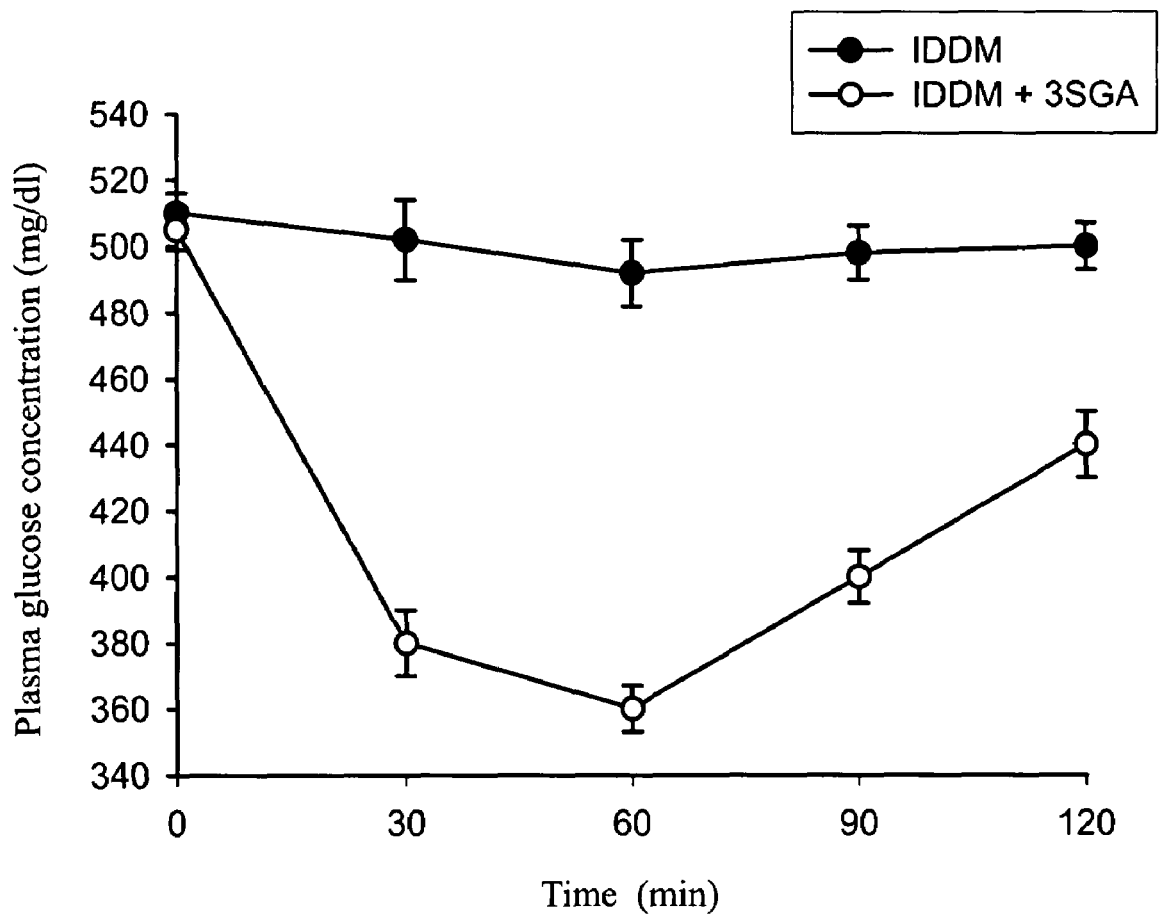
FIG. 3 is a diagram that shows changes in the plasma glucose levels of sick IDDM rats in relation to time after taking the 3SGA powder.

2. Changes in the plasma glucose levels of sick IDDM rats in relation to time after taking the 3SGA powder:

10 sick IDDM rats are fed with the 3SGA powder in dosages of 100 mg/kg BW, and the plasma glucose level of the rats is tested after 30, 60, 90, and 120 mins; the results are shown in FIG. 3.

It can be seen from FIG. 3 that the effect of lowering the plasma glucose level in the sick IDDM rats is the best 60 mins after taking the 3SGA powder.

3. Effects of normal SD rats and sick IDDM rats taking the 3SG powder or the 3SGA powder on glucose tolerance:

The normal SD rats are divided into three groups, and there are eight rats in each group; each rat is fed with the 3SG powder or the 3SGA powder of 100 mg/kg BW in dosage, or an equal volume of fresh water.

Figure 4:
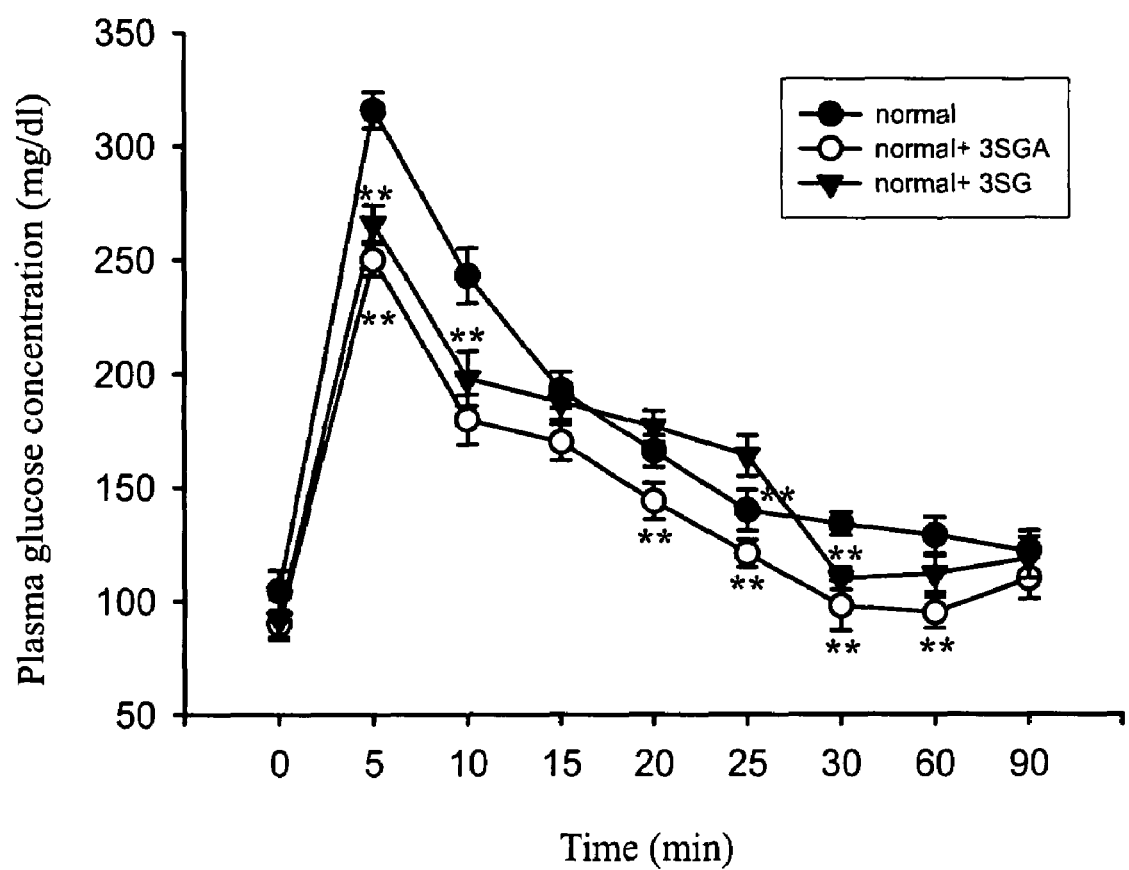
FIG. 4 is a diagram that shows the comparison of glucose tolerance between normal SD rats that had taken fresh water, 3SG powder, or 3SGA powder.

After one hour, the rats are injected with 60 mg/kg BW of glucose solution via intraperitoneal injection, and the levels of plasma glucose are tested by taking blood samples at 0, 5, 10, 15, 20, 25, 30, 60, and 90 mins, and the results are shown in FIG. 4.

From FIG. 4, it may be noted that after feeding the rats the 3SG powder and the 3SGA powder, the glucose tolerance of the normal SD rats is strengthened, and the effect of the 3SGA powder is stronger than that of the 3SG powder. The same experiment is carried out by using the sick IDDM rats, and the results are shown in FIG. 5.

Figure 5:
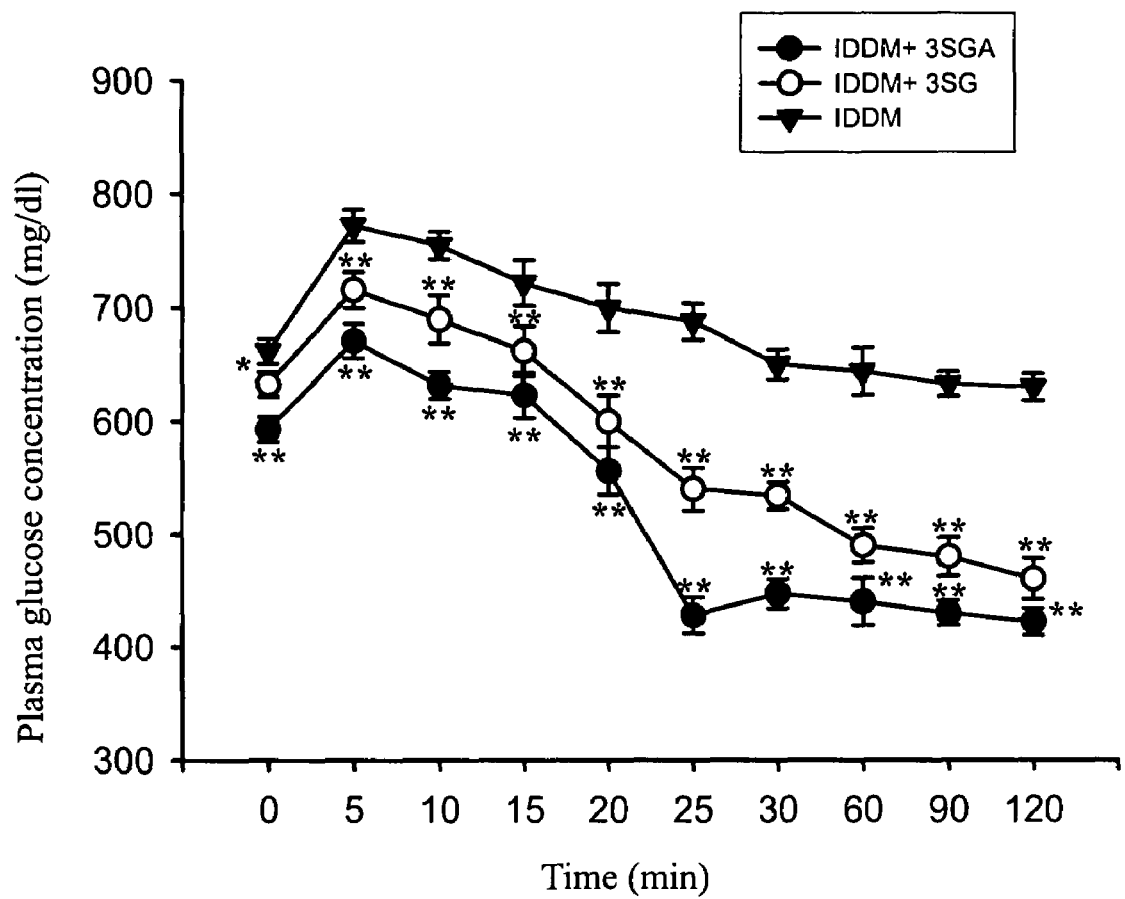
FIG. 5 is a diagram that shows the comparison of glucose tolerance between sick IDDM rats that had taken fresh water, 3SG powder, or 3SGA powder.

From FIG. 5, it should be noted that after feeding the rats the 3SG powder and the 3SGA powder, the glucose tolerance of the sick IDDM rats is enhanced, and the effect of the 3SGA powder is better than that of the 3SG powder.

4. Changes in the plasma glucose levels of normal C57BL/6 rats and sick NIDDM rats after taking the 3 SGA powder:

Each of the normal C57BL/6 rats and the sick NIDDM rats are divided into two groups; respectively, and there are eight rats in each group. One group of the sick NIDDM rats and the normal rats are fed with the 3SGA powder of 100 mg/kg BW in dosage, whereas the other group of the sick NIDDM rats and the normal rats are fed with an equal volume of fresh water. After 60 mins, blood samples are drawn from each group of rats to test the plasma glucose levels, the outcome is shown in FIG. 6.

Figure 6:
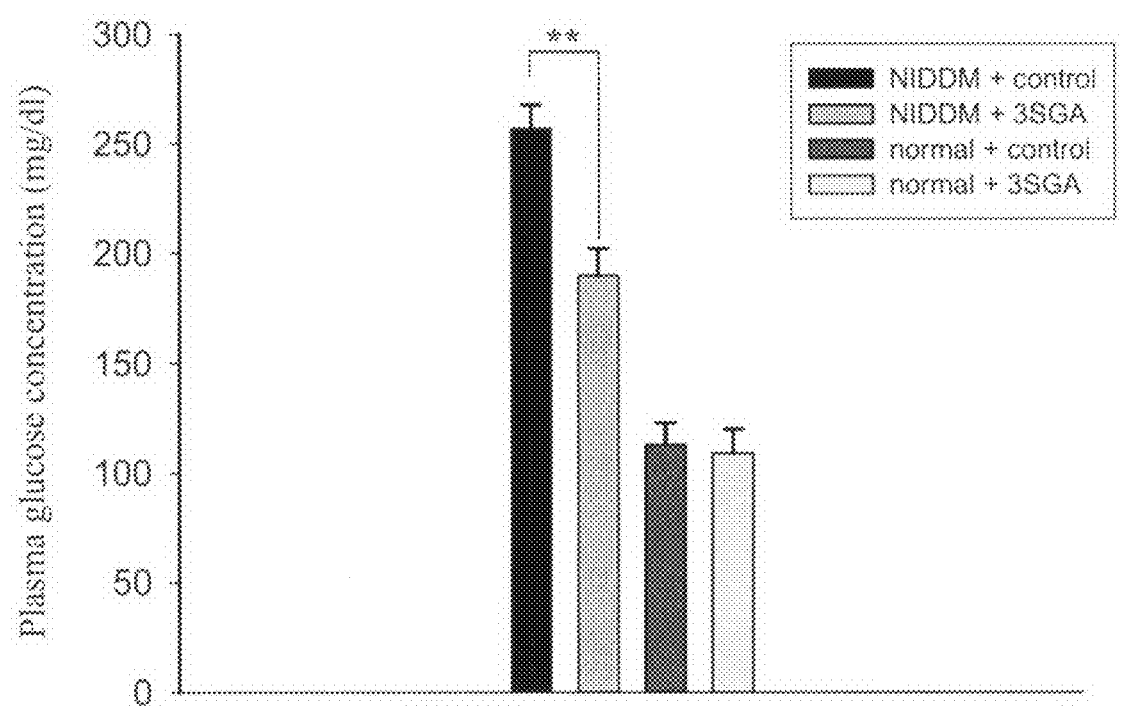
FIG. 6 is a diagram that shows the comparison of changes in the plasma glucose levels of normal C57BL/6 rats and sick NIDDM rats after taking 3SGA powder.

It may be observed from FIG. 6 that the plasma glucose level of the sick NIDDM rats dropped 26% at 60 mins after taking the 3SGA powder, but there is no significant change in the plasma glucose level of the normal rats.

5. Effect of the sick NIDDM rats taking the 3SGA powder on the glucose tolerance:

The sick NIDDM rats are divided into two groups, and there are eight rats in each group. The rats are fed with the 3SGA powder of 100 mg/kg BW in dosage or an equal volume of fresh water.

Figure 7:
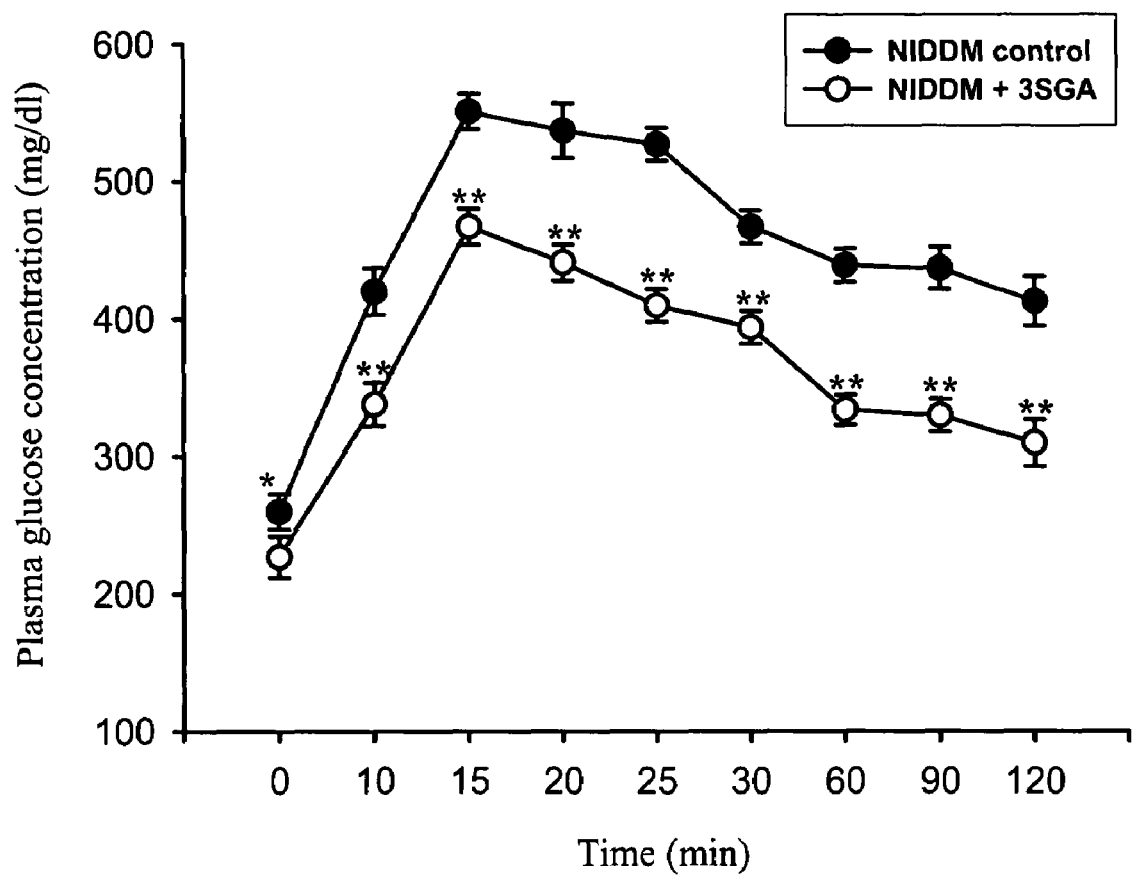
FIG. 7 is a diagram that shows the comparison of glucose tolerance in sick NIDDM rats after taking 3SGA powder.

The rats are fed with 1 g/kg BW of glucose solution 30 mins later, and then blood samples are taken from the rats at 0, 5, 10, 15, 20, 25, 30, 60, and 90 mins in order to test the plasma glucose level, the outcome is shown in FIG. 7.

From FIG. 7, it can be seen that after taking the 3SGA powder, the glucose tolerance of the sick NIDDM rats is significantly enhanced.

C. Long Term Tests

The results from the short term tests indicated that the feeding of the 3SGA powder achieved better effects than that of feeding the 3SG powder, thus only the 3SGA powder is used for carrying out the long term tests.

1. The plasma glucose and plasma triglyceride levels are lowered in the sick IDDM rats after taking the 3SGA powder:

The normal SD rats and the sick IDDM rats are divided into two groups; respectively, and each group has 10 rats. The rats are fed with the 3 SGA powder of 100 mg/kg BW in dosage or an equal volume of fresh water every 8 hours. Blood samples are taken every two days in order to test the levels of plasma glucose and plasma triglyceride. The blood samples are taken approximately 1 to 2 hours after the feeding of the 3SGA power.

Figure 8:
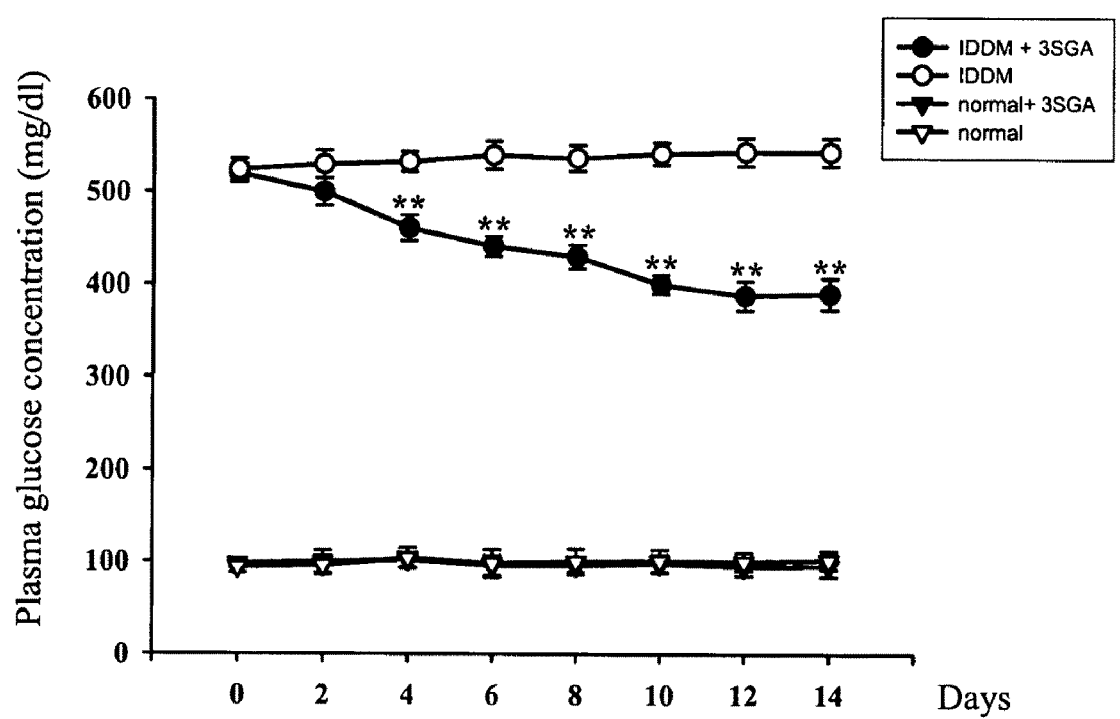
FIG. 8 is a diagram that shows the comparison of reduction in plasma glucose levels between normal SD rats and sick IDDM rats that took 3SGA powder for a period of time.
Figure 9:
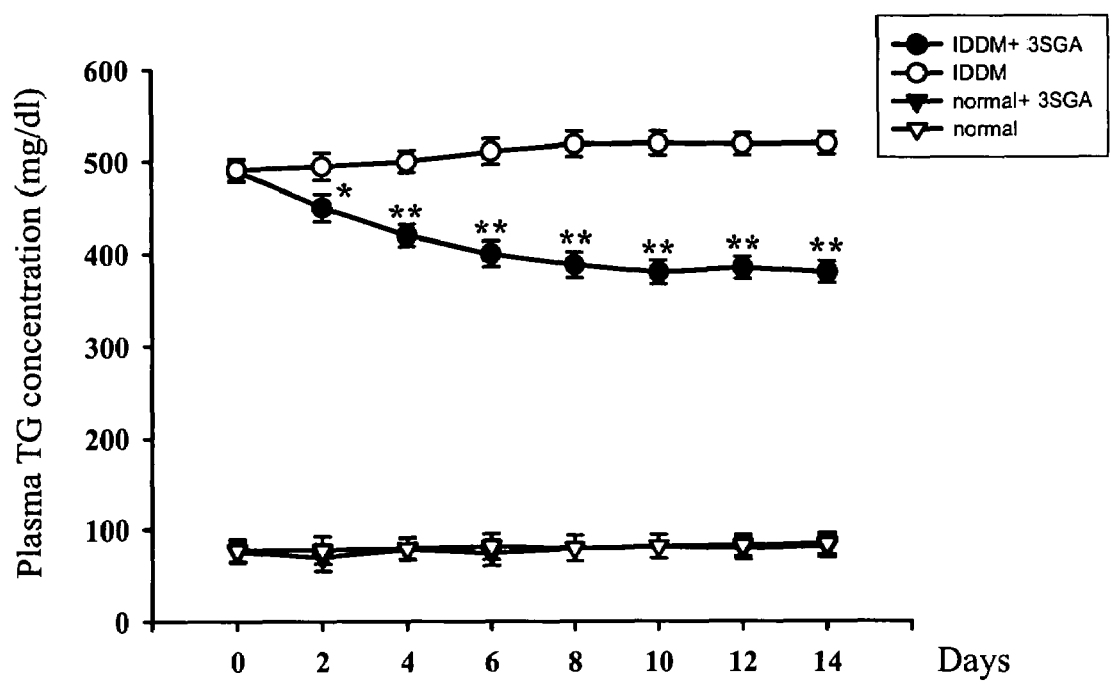
FIG. 9 is a diagram that shows the comparison of reduction in plasma triglyceride levels between normal SD rats and sick IDDM rats that took 3SGA powder for a period of time.

The reduction in plasma glucose levels in normal SD rats and sick IDDM rats that has taken the 3SGA powder for a period of time is shown in FIG. 8, while the reduction in plasma triglyceride levels in normal SD rats and sick IDDM rats that has taken the 3SGA powder for a period of time is shown in FIG. 9.

Comparing FIG. 8 with FIG. 9, it has been found that the levels of plasma glucose and plasma triglyceride of the sick IDDM rats were significantly reduced in the two weeks the rats were fed the 3SGA powder. However, there are no significant changes in the levels of plasma glucose and plasma triglyceride in the normal SD rats.

Figure 10:
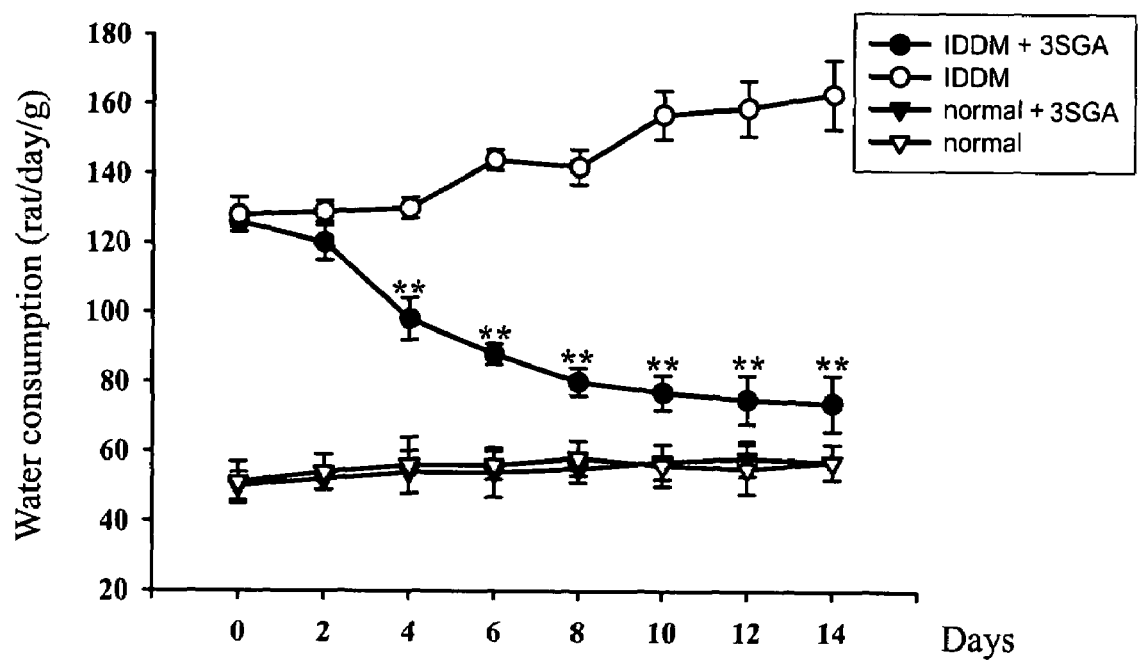
FIG. 10 is a diagram that shows whether the fluid intake has been lowered in normal SD rats and sick IDDM rats while taking 3SGA powder.

2. The sick IDDM rats showed decreased fluid intake after taking the 3SGA powder for a period of time:

When the normal SD rats and the sick IDDM rats are fed the 3SGA powder, the daily fluid intake of the normal SD rats and the sick IDDM rats is observed and measured, and the results are shown in FIG. 10.

From FIG. 10, it may be observed that there is significant reduction in the fluid intake of the sick IDDM rats when taking the 3SGA powder, but not for the normal SD rats.

Figure 11:
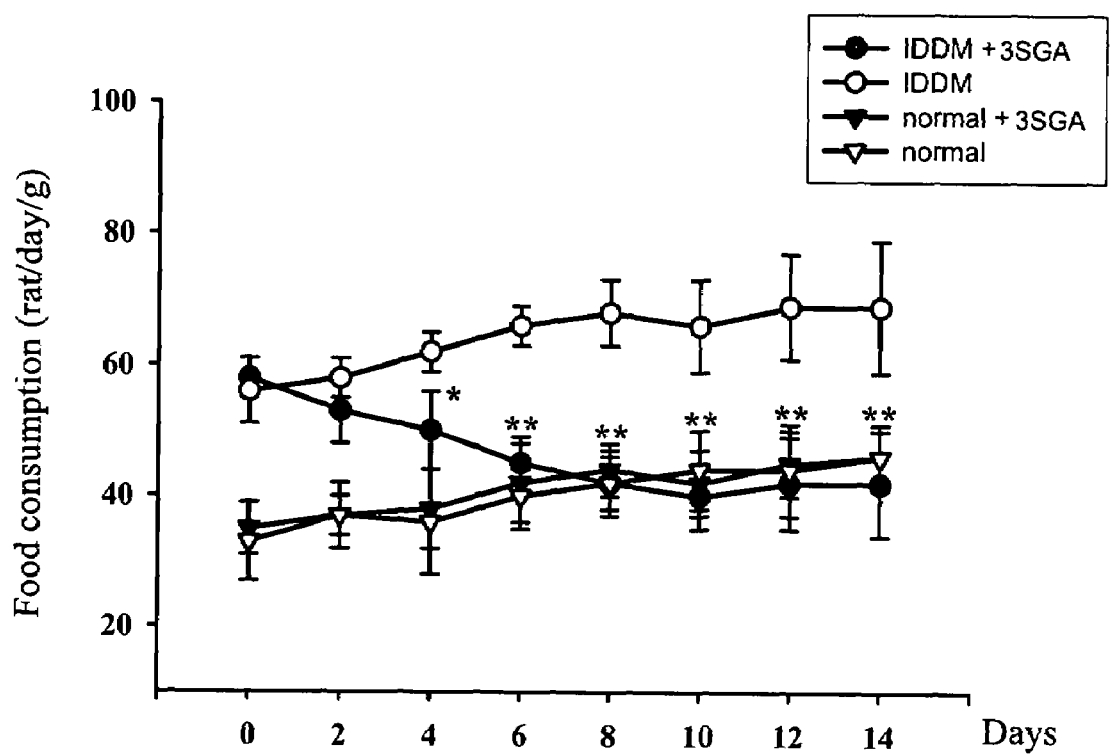
FIG. 11 is a diagram that shows whether the daily food intake has been lowered in normal SD rats and sick IDDM rats while taking 3SGA powder.

3. The sick IDDM rats showed decreased food intake after taking the 3SGA powder for a period of time:

When the normal SD rats and the sick IDDM rats are on the diet of the 3SGA powder, the daily food intake of the normal SD rats and the sick IDDM rats is observed and measured, and the results are shown in FIG. 11.

From FIG. 11, it may be noted that there is significant reduction in the food intake of the sick IDDM rats when taking the 3SGA powder, but not for the normal SD rats.

Figure 12:
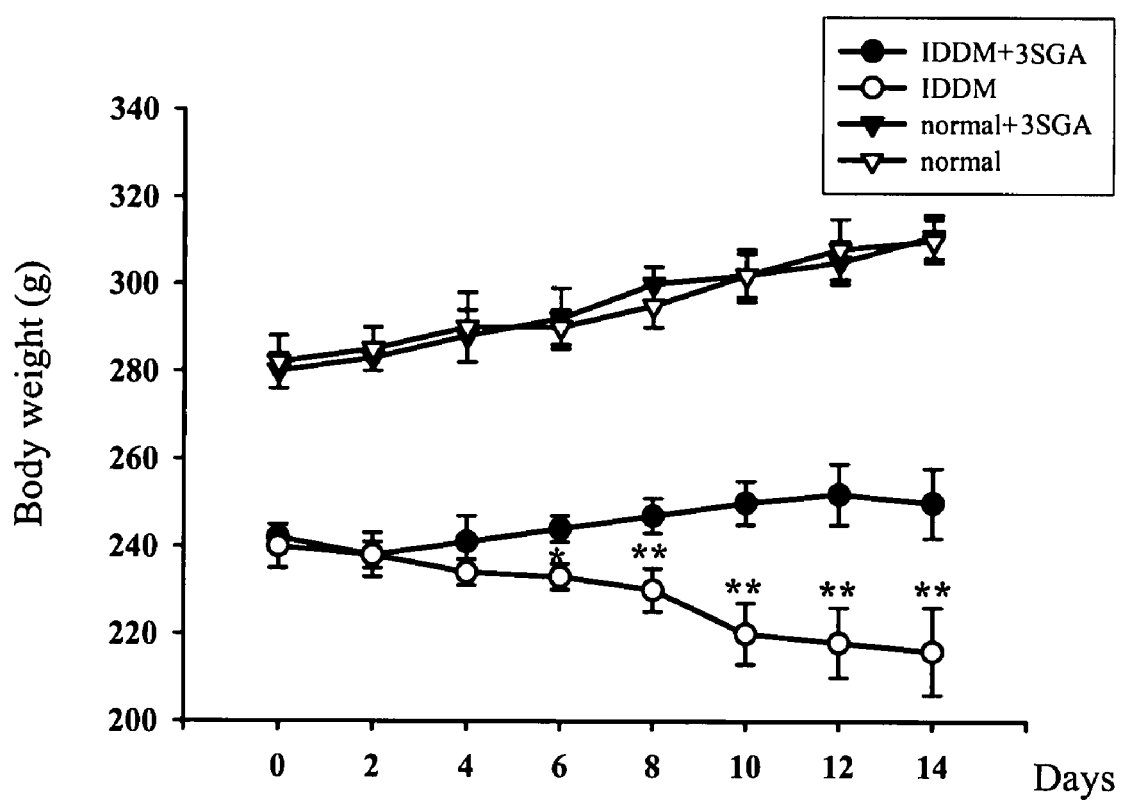
FIG. 12 is a diagram that shows changes in body weight of normal SD rats and sick IDDM rats while taking 3SGA powder.

4. Weight loss is effectively prevented in the sick IDDM rats taking the 3SGA powder for a period of time:

When the normal SD rats and the sick IDDM rats are on the diet of the 3SGA powder, changes in the weight of the normal SD rats and the sick IDDM rats are observed and measured, and the results are shown in FIG. 12.

From FIG. 12, it may be seen that weight loss is prevented in the sick IDDM rats taking the 3SGA powder, and the weight of the sick IDDM rats is increased slowly. Moreover, the growth of the normal SD rats taking the 3SGA powder is not affected.

Outcome:

Because flavonoids are allowed to be absorbed on the external surface of the 3SGA powder of the invention, and the 3SGA powder had been shown to be effective for lowering levels of plasma glucose and plasma triglyceride from the above-mentioned animal experiments, without any adverse side effects or toxicity. As a result, the 3SGA powder of the invention may be used as a health supplement for sufferers of diabetes, high plasma glucose, high plasma triglyceride, and metabolic disorders.

Although a preferred embodiment of the invention has been described for purposes of illustration, it is understood that various changes and modifications to the described embodiment can be carried out without departing from the scope and the spirit of the invention as disclosed in the appended claims.

What is claimed is:

1. A powdered health supplement having flavonoids absorbed onto the external surfaces of said powder and which is suitable for lowering plasma glucose and plasma triglyceride, and which is produced by a method comprising the following steps:

a. using a mixture of grape skin, grape seeds, grape stems, wherein the mixture is rinsed, dried and then ground into a powder after residual fruit fleshes and foreign substances have already been removed from the mixture;

b. adding 1 ml of 99.8% ethanol to every 1 g of the powder, and then the powder and ethanol are mixed together and stirred for 1 hour to release lipid-soluble flavonoids from cells in the powder; and c. allowing ethanol in the mixture resulting from the stirring in step (b) to completely evaporate, so that the flavonoids that have been released into the ethanol solution are adsorbed onto the external surfaces of the powder, thereby resulting in said powdered health supplement.

\* \* \* \* \*